United States Patent
O'hAimhirgin

(10) Patent No.: US 11,147,786 B2
(45) Date of Patent: *Oct. 19, 2021

(54) METHODS OF TREATING CHRONIC DRY EYE DISEASE USING C16:1N7-PALMITOLEATE AND DERIVATIVES THEREOF

(71) Applicant: Tersus Life Sciences, LLC, Bonita Springs, FL (US)

(72) Inventor: Lochlainn O'hAimhirgin, Mentor, OH (US)

(73) Assignee: TERSUS LIFE SCIENCES, LLC, Bonita Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/672,348

(22) Filed: Nov. 1, 2019

(65) Prior Publication Data

US 2020/0163921 A1    May 28, 2020

Related U.S. Application Data

(63) Continuation of application No. 16/354,036, filed on Mar. 14, 2019, now abandoned, which is a continuation of application No. 16/041,509, filed on Jul. 20, 2018, now abandoned, which is a continuation of application No. 15/830,991, filed on Dec. 4, 2017, now abandoned, which is a continuation of application No. 15/583,401, filed on May 1, 2017, now abandoned, which is a continuation of application No. 14/731,219, filed on Jun. 4, 2015, now Pat. No. 9,668,996.

(60) Provisional application No. 62/007,782, filed on Jun. 4, 2014, provisional application No. 62/008,489, filed on Jun. 5, 2014.

(51) Int. Cl.

| | | |
|---|---|---|
| *A61K 31/201* | (2006.01) | |
| *A61K 31/231* | (2006.01) | |
| *A61K 31/23* | (2006.01) | |
| *A61K 31/20* | (2006.01) | |
| *A61K 31/717* | (2006.01) | |
| *A61K 45/06* | (2006.01) | |
| *A61K 38/13* | (2006.01) | |

(52) U.S. Cl.
CPC ............ *A61K 31/201* (2013.01); *A61K 31/20* (2013.01); *A61K 31/23* (2013.01); *A61K 31/231* (2013.01); *A61K 31/717* (2013.01); *A61K 45/06* (2013.01); *A61K 38/13* (2013.01)

(58) Field of Classification Search
CPC .... A61K 31/201; A61K 31/231; A61K 31/20; A61K 31/717; A61K 45/06
See application file for complete search history.

(56) References Cited

U.S. PATENT DOCUMENTS

| | | | |
|---|---|---|---|
| 8,258,153 B2* | 9/2012 | Chappell | A61P 27/02 514/310 |
| 2011/0130457 A1* | 6/2011 | Borchman | A61P 27/04 514/549 |
| 2014/0024625 A1* | 1/2014 | Smith | A61K 31/593 514/167 |

* cited by examiner

*Primary Examiner* — Zohreh A Fay
(74) *Attorney, Agent, or Firm* — Tarolli, Sundheim, Covell & Tummino LLP

(57) ABSTRACT

The present technology provides methods for preventing or treating dry eyes in a subject in need thereof. The methods include administering to the subject an effective amount of a composition comprising C16:1n7-palmitoleate, its derivatives, pharmaceutically acceptable salts thereof, or a combination thereof.

15 Claims, 1 Drawing Sheet

OMEGA 7 TRIAL

Pt Name: _____ ID: _____
DOB: _____ Date: _____

Baseline/3month/6 month Visit

SPEED Score (≤6?): _____ (If less than 6 then excluded)

Lagophthalmos Y/N _____ Restasis Y/N (If either Yes then excluded)

Meibomian gland structure via Transillumination:

| Area of Loss: (See meiboscale) | Overall Impression of gland structure: |
|---|---|
| • 0 % = Degree 0<br>• <=25% = Degree 1<br>• 26%-50% = Degree 2<br>• 51%-75% = Degree 3<br>• >75% = Degree 4 | OD: Degree: 0  1  2  3  4  (If 3-4 excluded)<br><br>OS: Degree: 0  1  2  3  4  (If 3-4 excluded) |

LipiView Avg ICU: OD: _____ OS: _____    Partial Blink: OD: _____ OS: _____

Osmolarity (<308?): OD: _____ OS: _____    TBUT (>10?): OD: _____ OS: _____

Schirmer (>10?): OD: _____ OS: _____    VA CK: OD: _____ OS: _____

Lissamine Green: OD: _____ OS: _____    Fluress (SPK): OD: _____ OS: _____

MGE (Wipe Lid First)

| OD: | | | | OS: | | | |
|---|---|---|---|---|---|---|---|
| Temporal: | (Inspissated/solid) | 1 X ___ | = ___ | Temporal: | (Inspissated/solid) | 1 X ___ | = ___ |
| | (Cloudy, colored) | 2 X ___ | = ___ | | (Cloudy, colored) | 2 X ___ | = ___ |
| | (Clear) | 3 X ___ | = ___ | | (Clear) | 3 X ___ | = ___ |
| Central: | (Inspissated/solid) | 1 X ___ | = ___ | Central: | (Inspissated/solid) | 1 X ___ | = ___ |
| | (Cloudy, colored) | 2 X ___ | = ___ | | (Cloudy, colored) | 2 X ___ | = ___ |
| | (Clear) | 3 X ___ | = ___ | | (Clear) | 3 X ___ | = ___ |
| Nasal: | (Inspissated/solid) | 1 X ___ | = ___ | Nasal: | (Inspissated/solid) | 1 X ___ | = ___ |
| | (Cloudy, colored) | 2 X ___ | = ___ | | (Cloudy, colored) | 2 X ___ | = ___ |
| | (Clear) | 3 X ___ | = ___ | | (Clear) | 3 X ___ | = ___ |
| Total MGE Score (>18?): | | | | Total MGE Score (>18?): | | | |

| Line Of Marx to MG Orifices: | Line of Marx Evaluation: |
|---|---|
| 0 = LOM entirely posterior to MG Orifices,<br>1 = part of LOM touches MOs,<br>2 = LOM runs through all of the MOs,<br>3 = LOM is anterior to MO's | OD: 0  1  2  3<br>OS: 0  1  2  3 |

US 11,147,786 B2

METHODS OF TREATING CHRONIC DRY EYE DISEASE USING C16:1N7-PALMITOLEATE AND DERIVATIVES THEREOF

CROSS-REFERENCE TO RELATED APPLICATIONS

This application is a continuation of U.S. application Ser. No. 16/354,036 filed Mar. 14, 2019, which is a continuation of U.S. application Ser. No. 16/041,509, filed Jul. 20, 2018, which is a continuation of U.S. application Ser. No. 15/830,991, filed Dec. 4, 2017, which is a continuation of U.S. application Ser. No. 15/583,401, filed May 1, 2017, which is a continuation of U.S. application Ser. No. 14/731,219, filed Jun. 4, 2015, which claims the benefit of and priority to U.S. Application No. 62/007,782, filed Jun. 4, 2014, and U.S. Application No. 62/008,489, filed Jun. 5, 2014, the contents of which are incorporated herein by reference in their entireties.

BACKGROUND

The following description is provided to assist the understanding of the reader. None of the information provided or references cited is admitted to be prior art.

The term "dry eyes" includes, but is not limited to, dry eye disease, dry eye syndrome, or Chronic Dry Eye disease (CDE), is a condition in which there are insufficient tears to lubricate and nourish the eye. Tears are necessary for maintaining the health of the surface of the eye and for providing clear vision. With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose.

People with dry eyes either do not produce enough tears or have a poor quality of tears. Without enough tears, the film protecting the eye can break down, creating dry spots on the surface of the eye.

Dry eyes is a chronic disease that can be caused by advanced age, contact lens wear, certain medications, eye diseases, other medical conditions, or environmental factors. One type of dry eyes is caused by decreased tear production due to inflammation. Dry eyes are a common and often chronic problem, particularly in older adults.

SUMMARY

In one aspect, the present technology provide, a method for preventing or treating dry eyes in a subject in need thereof comprising administering to the subject an effective amount of a composition comprising one or more of C16:1n7-palmitoleate, a C16:1n7-palmitoleate derivative, a pharmaceutically acceptable salt thereof, or a combination thereof.

In some embodiments, the composition also includes a C16:0-palmitate, a C16:0-palmitate derivative, or a combination thereof.

In some embodiments, the composition also includes a C18:1n9-oleate, a C18:1n9-oleate derivative, or a combination thereof.

In some embodiments, the subject has been diagnosed with dry eyes or dry eye syndrome. In some embodiments, the subject is at risk for dry eyes or dry eye syndrome. In some embodiments, the subject is human.

In some embodiments, the method includes simultaneously, sequentially, or separately administrating at least one additional therapeutic agent, wherein the at least one additional therapeutic agent, is selected from the group consisting of cyclosporine ophthalmic emulsion, antibiotics, and hydroxypropyl cellulose insert.

In some embodiments of the method, the composition is administered orally, topically, systemically, intravenously, subcutaneously, intraperitoneally, or intramuscularly.

In some embodiments of the method, administration of the composition prevents, treats, or ameliorates one or more signs and/or symptoms of dry eyes. In some embodiments, the signs and/or symptoms are selected from the group consisting of stinging, burning, or scratchy sensation in the eyes, stringy mucus in or around the eyes, increased eye irritation from smoke or wind, eye fatigue, sensitivity to light, eye redness, sensation of foreign object in eyes, difficulty wearing contact lenses, periods of excessive tearing, swollen eyes, eye discomfort, eye pain, and blurred vision.

In some embodiments, the subject displays tear osmolarity less than 308 mOsms/L.

In some embodiments, the composition is administered daily for 4 weeks or more.

BRIEF DESCRIPTION OF THE DRAWINGS

FIG. 1 shows the patient data collection form that will be used while conducting the study described in Example 3.

DETAILED DESCRIPTION

It is to be appreciated that certain aspects, modes, embodiments, variations and features of the present technology are described below in various levels of detail in order to provide a substantial understanding of the present technology.

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a compound" includes a plurality of compounds.

As used herein, the terms "approximately" or "about" in reference to a number are generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of a composition, an agent, or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "composition" includes therapeutic and dietary formulations including, but not limited to, a dietary supplement, nutraceutical formulation, or pharmaceutical formulation. Compositions comprising C16:1n7-palmitoleate include, but are not limited to, dietary supplements, nutraceutical formulations, and pharmaceutical compositions. "Pharmaceutically acceptable composition" refers to a composition that is suitable for administration to a subject, particularly, a human. Such compositions include various excipients, diluents, carriers, and such other inactive agents well known to the skilled artisan. In another aspect, any of the pharmaceutical compositions, as described in the published U.S. Patent Application US 2012/0225941, incorporated herein by reference in its entirety, are provided where the pharmaceutical compositions include C16:1n7-palmitoleate or any derivatives thereof.

The methods described herein utilize compositions that include C16:1n7-palmitoleate or any one or more derivatives thereof as described in the published U.S. Patent Application US 2012/0225941, which is incorporated herein by reference in its entirety. In some embodiments, the C16:1n7-palmitoleate derivative is C16:1n7-palmitoleic acid. In some embodiments, the C16:1n7-palmitoleate derivative is cis-C16:1n7-palmitoleic acid. In some embodiments, the C16:1n7-palmitoleate derivative is a metal salt (e.g., $Na^+$, $K^+$, or Li) of cis-C16:1n7-palmitoleate. In some embodiments, the C16:1n7-palmitoleate derivative is an ester (e.g., ($C_1$-$C_8$) alkyl ester, methyl, ethyl, propyl, monoglyceride, diglyceride, triglyceride, or a combination thereof) of cis-C16:1n7-palmitoleate. In some embodiments, the C16:1n7-palmitoleate derivative is a methyl ester, ethyl ester, propyl ester of cis-C16:1n7-palmitoleate. In some embodiments, the cis-C16:1n7-palmitoleate ester is the ethyl ester.

The methods described herein are not limited to any particular chemical form of C16:1n7-palmitoleate and the compound may be given to subjects either as an ester, free acid or as a pharmaceutically acceptable salt.

As used herein, the term "effective amount" refers to a quantity sufficient to achieve a desired therapeutic and/or prophylactic effect, e.g., an amount which results in the prevention of, or a decrease in, dry eyes or CDE or one or more symptoms associated with dry eyes or CDE. In the context of therapeutic or prophylactic applications, the amount of a composition administered to the subject will depend on the type and severity of the disease and on the characteristics of the individual, such as general health, age, sex, body weight, tolerance to drugs, the degree, severity and type of disease or medical condition. The skilled artisan will be able to determine appropriate dosages depending on these and other factors. In some embodiments, the compositions are administered in combination with one or more additional therapeutic compounds. In some embodiments, C16:1n7-palmitoleate (or derivatives, pharmaceutically acceptable salts thereof, or a combination thereof) is administered to a subject having or suspected of having one or more signs or symptoms of dry eyes or CDE or to a subject at risk for dry eyes or CDE. By way of example, but not by way of limitation, a "therapeutically effective amount" of C16:1n7-palmitoleate (or derivatives, pharmaceutically acceptable salts thereof, or a combination thereof) means levels in which the physiological effects of the disease or medical condition giving rise to dry eyes or CDE are, at a minimum, ameliorated. In some embodiments, a therapeutically effective amount can be given in one or more administrations. In some embodiments, signs or symptoms of dry eyes or CDE include, but are not limited to, stinging, burning, or scratchy sensation in the eyes, stringy mucus in or around the eyes, increased eye irritation from smoke or wind, eye fatigue, sensitivity to light, eye redness, sensation of foreign object in eyes, difficulty wearing contact lenses, periods of excessive tearing, swollen eyes, eye discomfort, eye pain, and blurred vision (which worsens at the end of the day or after focusing for a prolonged period).

As used herein, the term "monoglyceride" refers to a fatty acid chain, such as C16:1n7-palmitoleate, covalently bonded to a glycerol molecule through an ester linkage. As used herein, the term "diglyceride" refers to a fatty acid chain, such as C16:1n7-palmitoleate, covalently bonded to a glycerol molecule through an ester linkage, wherein the glycerol molecule is further bonded to one additional fatty acid chain, which may or may not be C16:1n7-palmitoleate, though one additional ester linkage. As used herein, the term "triglyceride" refers to a fatty acid chain, such as C16:1n7-palmitoleate, covalently bonded to a glycerol molecule through an ester linkage, wherein the glycerol molecule is further bonded to two additional fatty acid chains, either or both of which may or may not be C16:1n7-palmitoleate, though two additional ester linkages.

As used herein, "prevention" or "preventing" of a disorder or condition refers to one or more compounds that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing dry eyes or CDE includes preventing the onset of dry eyes or CDE.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this definition.

As used herein, the terms "treating" or "treatment" or "alleviation" refers to both therapeutic treatment and prophylactic or preventative measures, wherein the object is to prevent or slow down (lessen) the targeted pathologic condition or disorder. For example, a subject is successfully "treated" for a disease or medical condition implicating dry eyes if, after receiving a therapeutic amount of C16:1n7-palmitoleate (or derivatives or pharmaceutically acceptable salts thereof) according to the methods described herein, the subject shows observable and/or measurable reduction in dry eyes. It is also to be appreciated that the various modes of treatment or prevention of medical diseases and conditions as described are intended to mean "substantial," which includes total but also less than total treatment or prevention, and wherein some biologically or medically relevant result is achieved.

General

Dry eye disease is a condition in which there are insufficient tears to lubricate and nourish the eyes. Tears are necessary for maintaining the health of the surface of the eyes and for providing clear vision. People with dry eyes either do not produce enough tears or have a poor quality of tears.

With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose. Dry eyes can result from an improper balance of tear production and drainage.

Inadequate amount of tears: Tears are produced by several glands in and around the eyelids. Tear production tends to diminish with age, with various medical conditions, or as a side effect of certain medicines. Environmental conditions such as wind and dry climates can also affect tear volume by increasing tear evaporation. When the normal amount of tear production decreases or tears evaporate too quickly from the eyes and symptoms of dry eye disease can develop.

Poor quality of tears: Tears are made up of three layers: oil, water, and mucus. Each component serves a function in protecting and nourishing the front surface of the eye. A smooth oil layer helps to prevent evaporation of the water layer, while the mucin layer functions in spreading the tears evenly over the surface of the eye. If the tears evaporate too quickly or do not spread evenly over the cornea due to deficiencies with any of the three tear layers, dry eye symptoms can develop.

The most common form of dry eyes is due to an inadequate amount of the water layer of tears. This condition, called keratoconjunctivitis sicca (KCS), is also referred to as dry eye syndrome.

People with dry eyes may experience symptoms of irritated, gritty, scratchy, or burning eyes, a feeling of something in their eyes, excess watering, and blurred vision. Advanced dry eyes may damage the front surface of the eye and impair vision.

Treatments for dry eyes aim to restore or maintain the normal amount of tears in the eyes to minimize dryness and related discomfort and to maintain eye health.

The present technology provides compositions and methods for preventing and treating dry eyes.

C16:1n7-palmitoleate Compositions

In some embodiments, the composition includes C16:1n7-palmitoleate, its derivatives, pharmaceutical salts thereof, or a combination thereof. Compositions that include C16:1n7-palmitoleate and its derivatives to be utilized in the methods described herein include any of those described in U.S. Pat. No. 8,703,818, which is incorporated herein by reference in its entirety.

By way of example, but not by way of limitation, in some embodiments the composition is a nutraceutical, a pharmaceutical, or a dietary supplement.

In some embodiments, the composition comprises about 1% to about 100% of C16:1n7-palmitoleate, its derivatives, pharmaceutically acceptable salts thereof, or a combination thereof relative to all of the components of the composition. In some embodiments, the composition comprises between about 5% to 20%, between about 20% to 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of C16:1n7-palmitoleate, its derivatives, pharmaceutically acceptable salts thereof, or a combination thereof relative to all of the components of the composition.

In some embodiments, the composition comprises a C16:1n7-palmitoleate derivative, wherein the wt % of the C16:1n7-palmitoleate derivative exceeds the wt % of any other single ingredient in the composition. In some embodiments, the composition comprises at least about 50 wt % of the C16:1n7-palmitoleate derivative. In some embodiments, the composition comprises at least about 60 wt % of the C16:1n7-palmitoleate derivative. In some embodiments, the composition comprises at least about 70 wt % of the C16:1n7-palmitoleate derivative. In some embodiments, the composition comprises at least about 80 wt % of the C16:1n7-palmitoleate derivative. In some embodiments, the composition comprises at least about 90 wt % of the C16:1n7-palmitoleate derivative.

Alternatively, or additionally, in some embodiments, the composition comprises between about 1% to 100% of C16:1n7-palmitoleate, its derivatives, pharmaceutically acceptable salts thereof, or a combination thereof relative to all of the fatty acids and fatty acid derivatives that are present in the composition. In some embodiments, the composition comprises between about 5% to 20%, between about 20% to 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 82%, 83%, 84%, 85%, 86%, 87%, 88%, 89%, 90%, 91%, 92%, 93%, 94%, 95%, 96%, 97%, 98%, or 99% of C16:1n7-palmitoleate, its derivatives, pharmaceutically acceptable salts thereof, or a combination thereof relative to all of the fatty acids and fatty acid derivatives that are present in the composition.

In some embodiments, the composition comprises C16:1n7-palmitoleate, its derivatives, pharmaceutically acceptable salts thereof, or a combination thereof and C16:0-palmitate, its derivatives, pharmaceutically acceptable salts thereof, or a combination thereof. In some embodiments, the ratio of C16:1n7-palmitoleate, its derivatives, pharmaceutically acceptable salts thereof, or a combination thereof to C16:0-palmitate, its derivatives, pharmaceutically acceptable salts thereof, or a combination thereof is equal to or greater than about 1:1. In some embodiments, the ratio of C16:1n7-palmitoleate, its derivatives, pharmaceutically acceptable salts thereof, or a combination thereof to C16:0-palmitate, its derivatives, pharmaceutically acceptable salts thereof, or a combination thereof (e.g., C16:1n7-palmitoleate:C16:0-palmitate) is about 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, 100:1, 200:1 or a ratio between any two of the ratios above.

In some embodiments, the composition comprises a C16:1n7-palmitoleate or its derivative and a C16:0-palmitate or its derivative, wherein the ratio of the C16:1n7-palmitoleate or its derivative to the C16:0-palmitate or its derivative (i.e., C16:1n7-palmitoleate:C16:0-palmitate) is between about 12:1 to about 100:1; and each C16:1n7-palmitoleate or its derivative and C16:0-palmitate or its derivative is independently selected from the group consisting of a free acid, pharmaceutically acceptable salt, (C$_1$-C$_8$) alkyl ester, monoglyceride, diglyceride, triglyceride and a combination thereof. In some embodiments, the ratio of the C16:1n7-palmitoleate or its derivative to the C16:0-palmitate or its derivative is between about 15:1 to 50:1. In some embodiments, the ratio of the C16:1n7-palmitoleate or its derivative to the C16:0-palmitate or its derivative is between about 50:1 to 100:1.

In some embodiments, all of the C16:1n7-palmitoleate or its derivative and C16:0-palmitate or its derivative are (C$_1$-C$_8$) alkyl esters. In some embodiments, all of the C16:1n7-palmitoleate or its derivative and C16:0-palmitate or its derivative are ethyl esters. In some embodiments, all of the C16:1n7-palmitoleate or its derivative and C16:0-palmitate or its derivatives are methyl esters. In some embodiments, all of the C16:1n7-palmitoleate or its derivative and C16:0-palmitate or its derivatives are propyl, butyl, pentyl, hexyl, heptyl or octyl esters. In some embodiments, all of the C16:1n7-palmitoleate or its derivative and C16:0-palmitate or its derivatives are free acids or pharmaceutically acceptable salts thereof. In some embodiments, all of the C16:1n7-palmitoleate or its derivative and C16:0-palmitate or its derivatives are selected from the group consisting of monoglycerides, diglycerides, triglycerides and combinations thereof. In some embodiments of the method, the C16:1n7-palmitoleate derivative is a cis-C16:1n7-palmitoleate derivative.

In some embodiments, the composition comprises C16:1n7-palmitoleate, its derivatives, pharmaceutically acceptable salts thereof, or a combination thereof and C18:1n9-oleate, its derivatives, pharmaceutically acceptable salts thereof, or a combination thereof. In some embodiments, the ratio of C16:1n7-palmitoleate, its derivatives, pharmaceutically acceptable salts thereof, or a combination thereof to C18:1n9-oleate, its derivatives, pharmaceutically acceptable salts thereof, or a combination thereof is equal to or greater than 1:1.

In some embodiments, the ratio of C16:1n7-palmitoleate, its derivatives, pharmaceutically acceptable salts thereof, or a combination thereof to C18:1n9-oleate, its derivatives, pharmaceutically acceptable salts thereof, or a combination thereof (e.g., C16:1n7-palmitoleate:C18:1n9-oleate) is between about 1.1:1 to about 100:1. In some embodiments, the ratio of C16:1n7-palmitoleate, its derivatives, pharmaceutically acceptable salts thereof, or a combination thereof to C18:1n9-oleate, its derivatives, pharmaceutically acceptable salts thereof, or a combination thereof is about 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, 100:1, 200:1 or a ratio between any two of the ratios recited above.

In some embodiments, the composition further comprises a C18:1n9-oleate or its derivative, wherein the ratio of the C16:1n7-palmitoleate or its derivative to the C18:1n9-oleate or its derivative, is between about 6:1 to 100:1, and each C18:1n9-oleate or its derivative is independently selected between the group consisting of a free acid, pharmaceutically acceptable salt, (C$_1$-C$_8$) alkyl ester, monoglyceride, diglyceride, triglyceride and a combination thereof. In some embodiments, the ratio of the C16:1n7-palmitoleate or its derivative to C18:1n9-oleate or its derivative is between about 10:1 to 20:1. In some embodiments, the ratio of the C16:1n7-palmitoleate or its derivative to the C18:1n9-oleate or its derivative is between about 20:1 to 50:1. In some embodiments, the ratio of the C16:1n7-palmitoleate or its derivative to C18:1n9-oleate or its derivative is between about 50:1 to 100:1.

In some embodiments, the composition contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight, palmitic acid, if any. In some embodiments, the composition contains substantially no palmitic acid. Alternatively, or additionally, in some embodiments, a composition contains no palmitic acid and/or derivative thereof.

C16:1n7-palmitoleate and derivatives thereof, can be obtained from any of the sources and methods described in U.S. Pat. No. 8,703,818, which is incorporated herein by reference in its entirety. By way of example, but by way of limitation, in some embodiments, C16:1n7-palmitoleate and derivatives thereof are isolated, concentrated, and/or purified from a source selected from the group consisting of one or more plants, animals, fish, and microorganisms.

In some embodiments, the C16:1n7-palmitoleate moiety of the C16:1n7-palmitoleate derivative is obtained from a source selected from the group consisting of fish, macadamia nuts, sea buckthorn, tallow, algae, bacteria, yeast, and a combination thereof.

In some embodiments, the C16:1n7-palmitoleate derivative comprises a C16:1n7-palmitoleate moiety that is obtained from fish. In some embodiments, the fish is selected from the group consisting of anchovies, menhaden, pollock, herring, cod, salmon, smelt, tuna, mackerel, krill and a combination thereof. In some embodiments, the fish is an anchovy. In other embodiments, the fish is menhaden.

Methods for Preventing or Treating Dry Eyes or Chronic Dry Eye Disease (CDE)

The present technology provides methods for preventing or treating dry eye in a subject comprising administering to the subject an effective amount of a composition comprising C16:1n7-palmitoleate, its derivatives, pharmaceutically acceptable salts thereof, or a combination thereof. In some embodiments, the method includes administering to the subject one or more of any one of the above embodiments of the composition.

The compositions comprising C16:1n7-palmitoleate, its derivatives, pharmaceutically acceptable salts thereof, or a combination thereof described herein are useful to prevent or treat dry eyes, chronic dry eye (CDE) disease, or dry eye syndrome. Dry eyes, chronic dry eye (CDE) disease, or dry eye syndrome is characterized by stinging, burning, or scratchy sensation in the eyes, stringy mucus in or around the eyes, increased eye irritation from smoke or wind, eye fatigue, sensitivity to light, eye redness, sensation of foreign object in eyes, difficulty wearing contact lenses, periods of excessive tearing, swollen eyes, eye discomfort, eye pain, and blurred vision (which worsens at the end of the day or after focusing for a prolonged period).

Compositions comprising C16:1n7-palmitoleate, its derivatives, pharmaceutically acceptable salts thereof, or a combination thereof, such as those described above, (e.g., C16:1n7-palmitoleate alone or C16:1n7-palmitoleate combined with C18:1n9-oleate) are useful in treating dry eyes, chronic dry eye (CDE) disease, or dry eye syndrome, as well as the signs, symptoms or complications of dry eyes, chronic dry eye (CDE) disease, or dry eye syndrome.

The disclosure also provides for both prophylactic and therapeutic methods of treating a subject having or at risk of (or susceptible to) dry eyes, chronic dry eye (CDE) disease, or dry eye syndrome and related complications. Accordingly, the present methods provide for the prevention and/or treatment of dry eyes, chronic dry eye (CDE) disease, or dry eye syndrome in a subject by administering an effective amount of a compositions comprising C16:1n7-palmitoleate, its derivatives, pharmaceutically acceptable salts thereof, or a combination thereof to a subject in need thereof.

Therapeutic Methods

The following discussion is presented by way of example only, and is not intended to be limiting.

One aspect of the present technology includes methods of treating dry eyes, chronic dry eye (CDE) disease, or dry eye syndrome in a subject in need thereof. One aspect of the present technology includes methods of treating dry eyes, chronic dry eye (CDE) disease, or dry eye syndrome in a subject diagnosed as having, suspected as having, or at risk of having, dry eyes, chronic dry eye (CDE) disease, or dry eye syndrome. In therapeutic applications, compositions or medicaments comprising C16:1n7-palmitoleate, its derivatives, pharmaceutically acceptable salts thereof, or a combination thereof are administered to a subject suspected of, or already suffering from dry eyes, chronic dry eye (CDE) disease, or dry eye syndrome in an amount sufficient to reduce the severity at least partially arrest or delay the onset of one or more of the symptoms of the disease, including its complications and intermediate pathological phenotypes in development of the disease.

Subjects suffering from dry eyes, chronic dry eye (CDE) disease, or dry eye syndrome can be identified by any or a combination of diagnostic or prognostic assays known in the art. For example, typical symptoms of dry eyes, chronic dry eye (CDE) disease, or dry eye syndrome include, but are not limited to, symptoms such as, e.g., stinging, burning, or scratchy sensation in the eyes, stringy mucus in or around the eyes, increased eye irritation from smoke or wind, eye fatigue, sensitivity to light, eye redness, sensation of foreign object in the eyes, difficulty wearing contact lenses, periods of excessive tearing, swollen eyes, eye discomfort, eye pain, and blurred vision (which worsens at the end of the day or after focusing for a prolonged period).

In some embodiments, dry eyes is diagnosed by tear osmolarity test. The tear osmolarity test measures the number of solid particles in a tear. The higher the tear osmolarity typically indicates that the tear has less water and more particles, e.g., salts, proteins, lipids, and mucin. A tear osmolarity score of below 308 mOsms/L is normal, 308-320 mOsms/L is mild dry eyes, 320-340 mOsms/L is moderate dry eyes, and above 340 mOsms/L is severe dry eye.

Prophylactic Methods

In one aspect, the present technology provides a method for preventing or delaying the onset of dry eyes, chronic dry eye (CDE) disease, or dry eye syndrome or symptoms of dry eyes, chronic dry eye (CDE) disease, or dry eye syndrome in a subject in need thereof. Subjects at risk for dry eyes, chronic dry eye (CDE) disease, or dry eye syndrome can be identified by, e.g., any or a combination of diagnostic or prognostic assays known in the art. In prophylactic applications, compositions or medicaments comprising C16:1n7-palmitoleate, its derivatives, pharmaceutically acceptable salts thereof, or a combination thereof are administered to a subject susceptible to, or otherwise at risk for dry eyes, chronic dry eye (CDE) disease, or dry eye syndrome in an amount sufficient to eliminate or reduce the risk, lessen the severity, or delay the outset of the dry eyes, chronic dry eye (CDE) disease, or dry eye syndrome, including biochemical, histologic and/or behavioral symptoms of the disease or disorder, its complications and intermediate pathological phenotypes presenting during development of the disease. Administration of a prophylactic compositions or medicaments comprising C16:1n7-palmitoleate, its derivatives, pharmaceutically acceptable salts thereof, or a combination thereof can occur prior to the manifestation of symptoms characteristic of the disease or disorder, such that the disease or disorder is prevented or, alternatively, delayed in its progression.

Subjects or at risk for dry eyes, chronic dry eye (CDE) disease, or dry eye syndrome may exhibit one or more of the following non-limiting risk factors: advanced age, wearing contact lens, taking certain medications, eye diseases, other medical conditions, or environmental factors.

In some embodiments the composition is administered as a nutraceutical, a pharmaceutical, or a dietary supplement.

In some embodiments, the subject is a mammal, a reptile, or an amphibian. In some embodiments, the mammal is any mammal, including, for example, farm animals, such as sheep, pigs, cows, and horses; pet animals, such as dogs and cats; laboratory animals, such as rats, mice and rabbits. In some embodiments, the mammal is a human.

Modes of Administration and Effective Dosages

Any method known to those in the art for contacting a cell, organ or tissue with the compositions of the present technology (i.e., C16:1n7-palmitoleate, its derivatives, pharmaceutically acceptable salts thereof, or combinations thereof) may be employed. Suitable methods include in vitro, ex vivo, or in vivo methods. In vivo methods typically include the administration of C16:1n7-palmitoleate or derivatives or pharmaceutically acceptable salts thereof, such as those described above, to a mammal, suitably a human. When used in vivo for therapy, C16:1n7-palmitoleate or derivatives or pharmaceutically acceptable salts thereof may be administered to the subject in effective amounts (i.e., amounts that have desired therapeutic effects). The dose and dosage regimen will depend upon the degree of the medical condition in the subject, the characteristics of C16:1n7-palmitoleate or derivatives or pharmaceutically acceptable salts thereof, e.g., its therapeutic index, the subject, and the subject's history.

The effective amount may be determined during pre-clinical trials and clinical trials by methods familiar to physicians and clinicians. An effective amount of C16:1n7-palmitoleate (or derivatives or pharmaceutically acceptable salts thereof) useful in the methods may be administered to a mammal in need thereof by any of a number of well-known methods for administering pharmaceutical compounds. In some embodiments, the composition comprising C16:1n7-palmitoleate (or its derivatives, pharmaceutically acceptable salts thereof, or combinations thereof) may be administered systemically or locally. In some embodiments, the composition comprising C16:1n7-palmitoleate (or its derivatives, pharmaceutically acceptable salts thereof, or combinations thereof) is administered orally, topically, systemically, intravenously, subcutaneously, intraperitoneally, or intramuscularly.

In some embodiments, C16:1n7-palmitoleate (or derivatives thereof) may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate, tartrate or trifluoroacetate salt.

In some embodiments, C16:1n7-palmitoleate, its derivatives, pharmaceutically acceptable salts thereof, or combinations thereof described herein can be incorporated into pharmaceutical compositions for administration, alone or in combination, to a subject for the treatment or prevention of joint pain. Such compositions typically include the active agent (e.g., C16:1n7-palmitoleate) and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

Compositions containing C16:1n7-palmitoleate (or its derivatives, pharmaceutically acceptable salts thereof, or combinations thereof) can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, isotonic agents are included, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active compound plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

By way of example, but not by way of limitation, in some embodiments, administration by inhalation, C16:1n7-palmitoleate (or its derivatives, pharmaceutically acceptable salts thereof, or combinations thereof) is delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of C16:1n7-palmitoleate (its derivatives, pharmaceutically acceptable salts thereof, or combinations thereof) as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. By way of example, but not by way of limitation, in some embodiments, transmucosal administration is accomplished through the use of nasal sprays. For transdermal administration, the active compounds are formulated into ointments, salves, gels, or creams as generally known in the art. In some embodiments, transdermal administration is performed by iontophoresis.

In some embodiments, C16:1n7-palmitoleate (or its derivatives, pharmaceutically acceptable salts thereof, or combinations thereof) is formulated in a carrier system. In some embodiments, the carrier is a colloidal system. By way of example, but not by way of limitation, colloidal systems include, but is not limited to, a liposome or a phospholipid bilayer vehicle. One skilled in the art would appreciate that there are a variety of methods to prepare liposomes. See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8):915-923 (2000)). In some embodiments, an active agent is also loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In some embodiments, C16:1n7-palmitoleate (or its derivatives, pharmaceutically acceptable salts thereof, or combinations thereof) is embedded in the polymer matrix. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.).

In some embodiments, C16:1n7-palmitoleate (or, its derivatives, pharmaceutically acceptable salts thereof, or combinations thereof) are prepared with carriers that will protect C16:1n7-palmitoleate (or, its derivatives, pharmaceutically acceptable salts thereof, or combinations thereof) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. C16:1n7-palmitoleate (or its derivatives, pharmaceutically acceptable salts thereof, or combinations thereof) can also be formulated to enhance intracellular delivery.

Dosage, toxicity and therapeutic efficacy of C16:1n7-palmitoleate (or its derivatives, pharmaceutically acceptable salts thereof, or combinations thereof) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, C16:1n7-palmitoleate, its derivatives, pharmaceutically acceptable salts thereof, or combinations thereof, exhibit high therapeutic indices.

The dosage of such compounds lies within a range of circulating concentrations that include the ED50 with little or no toxicity. The dosage may vary within this range depending upon the dosage form employed and the route of administration utilized. For C16:1n7-palmitoleate (or its derivatives, pharmaceutically acceptable salts thereof, or combinations thereof) used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

In some embodiments, an effective amount of C16:1n7-palmitoleate, its derivatives, pharmaceutically acceptable salts thereof, or combinations thereof, ranges between about 0.000001 mg per kilogram body weight per day to about 10,000 mg per kilogram body weight per day. In some embodiments, the dosage ranges are between about 0.0001 mg per kilogram body weight per day to about 100 mg per kilogram body weight per day. By way of example, but not by way of limitation, in some embodiments, dosages are between about 1 to 10, between about 2 to 8, or between about 4-6 mg/kg body weight every day, every two days or every three days. In some embodiments, dosages are between about 1 to 10, between about 2 to 8, or between about 4-6 mg/kg body weight every week, every two weeks or every three weeks.

In some embodiments, a single dosage of C16:1n7-palmitoleate, its derivatives, pharmaceutically acceptable salts thereof, or combinations thereof, ranges between about 0.001-10,000, between about 0.01-7,500, between about 0.1-5,000, between about 1.0-2,500, between about 10-1,000, between about 50-750, between about 100-500, or between about 150-250 micrograms per kg body weight. In some embodiment, concentrations of C16:1n7-palmitoleate, its derivatives, pharmaceutically acceptable salts thereof, or combinations thereof, in a carrier ranges between about 0.2 to 2000, between about 0.1-1500, between about 1.0-1000, between about 10-750, between about 50-500, between about 100-250, or between about 125-200 micrograms per delivered milliliter.

In some embodiments, an effective amount of C16:1n7-palmitoleate, its derivatives, pharmaceutically acceptable salts thereof, or combinations thereof, ranges between about 1 to 1000 mg, between about 10 to 900 mg, between about 20 to 800 mg, between about 30 to 700, between about 40 to 600 mg, between about 50 to 500 mg, between about 60 to 400, between about 70 to 300, between about 80 to 200 mg, or between about 90 to 100 mg. In some embodiments, an effective amount of C16:1n7-palmitoleate, its derivatives, pharmaceutically acceptable salts thereof, or combinations thereof is more than about 1000 mg.

By way of example, but not by way of limitation, in some embodiments a treatment regime entails administration once per day, once a week, twice a week, three times a week, four times a week, five times a week, or six times a week. In some embodiments, any of the above treatment regimes is performed for between 1 to 12 weeks, between 2 to 11 weeks, between 3 to 10 weeks, between 4 to 9 weeks, between 5 to 7 weeks, or more than 12 weeks. In some embodiments, any of the above treatment regimes is performed for between 1 to 12 months, between 2 to 11 months, between 3 to 10 months, between 4 to 9 months, between 5 to 7 months, or more than 12 months.

In some embodiments, a therapeutically effective amount of C16:1n7-palmitoleate, its derivatives, pharmaceutically acceptable salts thereof, or combinations thereof, is defined as a concentration of C16:1n7-palmitoleate, its derivatives, pharmaceutically acceptable salts thereof, or combinations thereof, at the target tissue between about $10^{-12}$ to $10^{-6}$ molar, e.g., approximately $10^{-7}$ molar. In some embodiments, C16:1n7-palmitoleate, its derivatives, pharmaceutically acceptable salts thereof, or combinations thereof, is delivered by systemic doses between about 0.001 to 100 mg/kg, or between about 0.01 to 75 mg/kg, or between about 0.1 to 50 mg/kg, or between about 1.0 to 25 mg/kg, or equivalent dose by body surface area. In some embodiments, the schedule of doses would be optimized to maintain the therapeutic concentration at the target tissue. In some embodiments, the doses are administered by single daily or weekly administration, but may also include continuous administration (e.g., parenteral infusion or transdermal application).

In some embodiments, the dosage of C16:1n7-palmitoleate, its derivatives, pharmaceutically acceptable salts thereof, or combinations thereof, is provided at a "low," "mid," or "high" dose level. In some embodiments, the low dose is provided between about 0.0001 to 0.5 mg/kg/h or between about 0.001 to 0.1 mg/kg/h. In some embodiments, the mid-dose is provided between about 0.01 to 1.0 mg/kg/h or between about 0.01 to 0.5 mg/kg/h. In some embodiments, the high dose is provided between about 0.5 to 10 mg/kg/h or between about 0.5 to 2 mg/kg/h.

In some embodiments, a high dosage at short intervals is sometimes required until progression of the medical condition is reduced or terminated, and until the subject shows partial or complete amelioration of symptoms of the medical condition. Thereafter, the patient is administered a prophylactic regime.

In some embodiments, C16:1n7-palmitoleate, its derivatives, pharmaceutically acceptable salts thereof, or combinations thereof, are administered in an amount that achieves a serum concentration between about 100 ng/ml to 9000 ng/ml. In some embodiments, C16:1n7-palmitoleate, its derivatives, pharmaceutically acceptable salts thereof, or combinations thereof, are administered in an amount that achieves a serum concentration between about 100 ng/ml to 1000 ng/ml. In some embodiments, the serum concentration achieved is between about 300 ng/ml to 500 ng/ml, between about 100 ng/ml to 500 ng/ml, between about 500 ng/ml to 1000 ng/ml, between about 1000 ng/ml to 1500 ng/ml, between about 500 ng/ml to 1500 ng/ml, between about 1000 ng/ml to 2000 ng/ml, between about 1500 ng/ml to 2000 ng/ml, between about 2000 ng/ml to 3000 ng/ml, between about 2000 ng/ml to 2500 ng/ml, between about 2500 ng/ml to 3000 ng/ml, between about 3000 ng/ml to 4000 ng/ml, between about 3000 ng/ml to 3500 ng/ml, between about 3500 ng/ml to 4000 ng/ml, between about 4000 ng/ml to 5000 ng/ml, between about 4000 ng/ml to 4500 ng/ml, between about 4500 ng/ml to 5000 ng/ml, between about 5000 ng/ml to 6000 ng/ml, between about 5000 ng/ml to 5500 ng/ml, between about 5500 ng/ml to 6000 ng/ml, between about 6000 ng/ml to 7000 ng/ml, between about 7000 ng/ml to 8000 ng/ml, or between about 8000 ng/ml to 9000 ng/ml.

The skilled artisan will appreciate that certain factors may influence the dosage and timing required to effectively treat a subject, including but not limited to, the severity of the medical disease or condition, previous treatments, the general health and/or age of the subject, and other diseases present. Moreover, treatment of a subject with a therapeutically effective amount of the therapeutic compositions described herein can include a single treatment or a series of treatments.

In some embodiments, C16:1n7-palmitoleate, its derivatives, pharmaceutically acceptable salts thereof, or combinations thereof, are formulated as a pharmaceutical composition within a soft gelatin capsule. In some embodiments, the soft gelatin capsule includes about 0.5 grams, about 1 gram, about 1.5 grams, or about 2 grams of the pharmaceutical composition comprising at least 20%, at least 30%, at least 40%, at least 50%, at least 60%, at least 70%, at least 80% or at least 90% of C16:1n7-palmitoleate, or a derivative or pharmaceutically acceptable salt thereof. In some embodiments, one capsule per day is administered to a subject for the treatment or prevention of any of the conditions, such as dry eyes, as described herein. In some embodiments, two capsules per day are administered to the subject. In some embodiments, two to ten capsules per day are administered to the subject.

In some embodiments, the subject is a mammal, a reptile, or an amphibian. In some embodiments, the mammal is any mammal, including, for example, farm animals, such as sheep, pigs, cows, and horses; pet animals, such as dogs and cats; laboratory animals, such as rats, mice and rabbits. In some embodiments, the mammal is a human.

Combination Therapy with C16:1n7-Palmitoleate and Other Therapeutic Agents

In some embodiments, C16:1n7-palmitoleate, its derivatives, pharmaceutically acceptable salts thereof, or combinations thereof, may be combined with one or more additional therapeutic agents for the prevention or treatment of dry eyes, e.g., dry eye syndrome. By way of example, but not by way of limitation, treatment for dry eyes, e.g., dry eye syndrome, can include, in addition to C16:1n7-palmitoleate, its derivatives, pharmaceutically acceptable salts thereof, or combinations thereof, but is not limited to, Restasis® (cyclosporine ophthalmic emulsion) (Sandimmun, United Kingdom), antibiotics, and hydroxypropyl cellulose insert (e.g., Lacrisert®(Valeant Pharmaceuticals, Bridgewater, N.J.)).

In some embodiments, an additional therapeutic agent is administered to a subject in combination with C16:1n7-palmitoleate, its derivatives, pharmaceutically acceptable salts thereof, or combinations thereof, such that a synergistic therapeutic effect is produced. Therefore, lower doses of one or both of the therapeutic agents may be used in treating dry eyes, e.g., dry eye syndrome, resulting in increased therapeutic efficacy and decreased side-effects.

In any case, the multiple therapeutic agents may be administered in any order, e.g., sequentially or separately or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary between more than zero weeks to less than four weeks. In addition, the combination methods, compositions and formulations are not to be limited to the use of only two agents.

EXAMPLES

The present technology is further illustrated by the following examples, which should not be construed as limiting in any way. For each of the examples below, C16:1n7-palmitoleate, its derivatives, pharmaceutically acceptable salts thereof, or combinations thereof could be used.

Example 1: C16:1n7-palmitoleate in Treating Dry Eyes in Human Subjects

This Example shows the treatment of dry eyes using a composition comprising C16:1n7-palmitoleate, its derivatives, pharmaceutically acceptable salts thereof, or combinations thereof.

Patients diagnosed with dry eye disease (as determined by having tear osmolarity over 308 mOsms/L, which is the clinical minimum for dry eyes, per eye) were treated daily with a dietary supplement containing 210 mg of C16:1n7-palmitoleate for 30 days.

Tear osmolarity for left and right eyes were scored at day 1 and day 30, see Table 1. A tear osmolarity score of below 308 mOsms/L is normal, 308-320 mOsms/L is mild dry eyes, 320-340 mOsms/L is moderate dry eyes, and above 340 mOsms/L is severe dry eye. At day 30, patients also ranked their feeling of improvement of dry eye on a scale of 1-10, see Table 1.

TABLE 1

Treatment of Dry Eyes with C16:1n7-palmitoleate

| Patient | Sex | Age | Tear Osmolarity Day 1 (mOsms/L) | Tear Osmolarity Day 30 (mOsms/L) | Symptom Improvement (Scale of 1-10) |
|---|---|---|---|---|---|
| 1 | Male | 69 | Left eye 347 | Left eye 308 | 8 |
| | | | Right eye 367 | Right eye 310 | |
| 2 | Male | 54 | Left eye 332 | Left eye 313 | 3 |
| | | | Right eye 362 | Right eye 314 | |
| 3 | Female | 40 | Left eye 294 | Left eye 300 | 4 |
| | | | Right eye 305 | Right eye 300 | |
| 4 | Female | 33 | Left eye 333 | Left eye 302 | 7 |
| | | | Right eye 340 | Right eye 308 | |
| 5 | Female | 83 | Left eye 312 | Left eye 293 | 7 |
| | | | Right eye 382 | Right eye 302 | |
| 6 | Female | 56 | Left eye 351 | Left eye 314 | 6 |
| | | | Right eye 325 | Right eye 299 | |
| 7 | Female | 48 | Left eye 322 | Left eye 302 | 4 |
| | | | Right eye 341 | Right eye 307 | |
| 8 | Female | 44 | Left eye 314 | Left eye 301 | 6 |
| | | | Right eye 328 | Right eye 367 | |

The results show that administration of the C16:1n7-palmitoleate dietary supplement reduced dry eyes based on tear osmolarity score. For example, patients that initially exhibited at least one severe dry eye, i.e., patients 1, 2, 5, and 7, exhibited normal or very mild dry eyes after 30 days of treatment with the C16:1n7-palmitoleate, see Table 1.

Additionally, a majority of the patients reported that their eyes felt better after the 30 day treatment with the C16:1n7-palmitoleate nutraceutical, see Table 1.

These results show that compositions comprising C16:1n7-palmitoleate, its derivatives, pharmaceutically acceptable salts thereof, or combinations thereof, are useful in treating dry eyes.

Example 2: C16:1n7-palmitoleate Ameliorates Meibomian Gland Dysfunction in Human Subjects Meibomian gland dysfunction (MGD) is thought to be the leading cause of dry eye disease. This Example demonstrates that compositions comprising C16:1n7-palmitoleate, its derivatives, pharmaceutically acceptable salts thereof, or combinations thereof are useful in ameliorating or treating MGD in subjects with dry eye symptoms.

Twenty nine patients, each diagnosed as having moderate to severe dry eye symptoms/MGD, were selected for the study.

Patients were classified as having none, mild, or moderate meibomian gland secretion blockage by evaluating the secretion of the meibomian glands in the nasal, central, and temporal regions of the lower eyelid. MGD was scored using a 0-4 grading scale, 4 correlating with severe dysfunction. A summary of the grading scale is provided below:

1=meibomian glands in all 3 regions secreting/cloudy
   2=meibomian glands in 2 out of 3 regions secreting/cloudy
   3=meibomian glands in 1 out of 3 regions secreting/cloudy
   4=no observable meibomian gland secretion in any of the 3 regions 2+ and 2,3 are used interchangeably and mean more than ⅔<1.

After the initial baseline evaluation, patients received daily doses of a dietary supplement containing 210 mg of C16:1n7-palmitoleate for over 30 days.

Tear osmolarity (TL) and MGD for left and right eyes (LE and RE respectively) were scored at Day 0 (baseline evaluation) and at the follow-up visit (FV), see Table 2. A tear osmolarity score of below 308 mOsms/L is normal, 308-320 mOsms/L is mild dry eyes, 320-340 mOsms/L is moderate dry eyes, and above 340 mOsms/L is severe dry eye. The terms 'above' and 'below' refer to values above and below the detectable range of the Tearlab diagnostic device respectively. Patients also recorded their comments regarding perceived improvements of their dry eye symptoms. Table 2.

TABLE 2

Improvement of MGD with C16:1n7-palmitoleate

| Patient | Day 0 TL RE | Day 0 TL LE | Day 0 MGD RE | Day 0 MGD LE | FV TL RE | FV TL LE | FV MGD RE | FV MGD LE | Comment |
|---|---|---|---|---|---|---|---|---|---|
| 1 | 303 | 323 | 4 | 4 | 308 | 306 | 4 | 1 | good |
| 2 | 351 | 327 | 3 | 3 | 311 | 303 | 3 | 3 | good |
| 3 | 329 | 314 | 2+ | 2+ | 235 | 299 | 2 | 2 | good |
| 4 | 321 | 311 | 3 | 2 | 284 | 317 | 1 | 1 | great |
| 5 | 316 | 307 | 4 | 4 | 302 | 298 | 3 | 3 | good |
| 6 | 357 | 349 | 2+ | 2+ | 301 | 303 | 1 | 1 | good |
| 7 | 311 | 312 | 4 | 4 | 295 | 291 | 3 | 3 | good |
| 8 | 326 | 307 | 3+ | 3+ | 307 | 310 | 2+ | 3 | good |
| 9 | 329 | 314 | 3+ | 3+ | 304 | 316 | 2 | 2 | good |
| 10 | 383 | above | 2, 3 | 2, 3 | 307 | 314 | 1, | 1, | good |
| 11 |  |  | 4 | 4 | 302 | 299 | 1 | 1 | great |
| 12 | 335 | 324 | 4 | 4 | 348 | 354 | 1 | 1 | good |
| 13 | below | 339 | 3 | 3 | 354 | 352 | 1 | 1 | good |
| 14 | 330 | 308 | 3 | 3 | 352 | 330 | 3 | 2+ | poor |
| 15 | 318 | 364 | 3 | 3 | 345 | 324 | 1 | 2 | good |
| 16 | 337 | 361 | 4 | 4 |  |  | 2 | 2 | good |
| 17 | 324 | 317 | 4 | 4 | 309 | 331 | 4 | 4 | good |
| 18 |  |  | 4 | 4 |  |  | 4 | 4 | Better |
| 19 | 330 | above | 4 | 4 | 314 | 327 | 4 | 4 | good |
| 20 | 313 | 314 | 3 | 3 |  |  | 0 | 0 | great |
| 21 | 290 | 364 | 2 | 2 | 318 | 300 | 1 | 1 | great |
| 22 | 293 | 302 | 4 | 4 | 355 | above | 1 | 1 |  |
| 23 | 235 | 326 | 4 | 4 | 318 | 305 | 4 | 4 | happy |
| 24 | 348 | 356 | 4 | 4 |  |  | 2 | 2 | happy |
| 25 | 310 | 320 | 3 | 3 | below | below | 2 | 2 | good |
| 26 | 301 | 313 | 4 | 4 | 302 | 308 |  |  | good |
| 27 | 322 | 358 | 4 | 4 | below | below | 2 | 2 | good |
| 28 | 308 | 349 | 3 | 3 | 294 | 323 | 1 | 3 | good |
| 29 | 360 | 317 | 3 | 3 | 303 | 311 | 3 | 3 | better |

The results show that administration of the C16:1n7-palmitoleate dietary supplement resulted in the improvement of tear osmolarity scores and/or MGD scores. For example, patients that initially exhibited severe MGD scores, e.g., patients 1, 4-7, 11-13, 15-16, 20-22, 24 and 27, showed improvement in MG secretion after treatment with the C16:1n7-palmitoleate, see Table 2.

Additionally, a majority of the patients reported that their eyes felt better after treatment with the C16:1n7-palmitoleate dietary supplement, see Table 2.

These results show that compositions comprising C16:1n7-palmitoleate, its derivatives, pharmaceutically acceptable salts thereof, or combinations thereof, are useful in improving MGD scores in subjects with dry eye symptoms.

Example 3: C16:1n7-palmitoleate Reduces Meibomian Gland Atrophy in Human Subjects Patient Selection:

All prospective patients will be instructed to cease using any preexisting dry eye or blepharitis therapy prior to any baseline evaluation (e.g., punctal plugs, lid hygiene products, warm compresses, and artificial tears). One hundred (100) patients, each having moderate to severe dry eye symptoms/MGD, shall be selected after being subjected to testing for oil gland expression, lissamine green staining of lids and conjunctiva, tear break-up time testing, Tearlab Osmolarity analysis of both eyes, and Schirmer's aqueous testing with and without anesthesia. These patients will also complete questionnaires that are specifically designed for the present study.

A standardized MGE device (MGE) will be used to classify patients as having none, mild, or moderate meibomian gland secretion blockage. LipiView Diagnostics (TearSciences), which includes interferometric scanning and meibography will be used to assess the following endpoints: Meibomian Gland Atrophy and Structure, Lipid Layer Thickness (LLT), Blink Rate, and Blink Closure Quality. The patients shall be separated into four groups according to the varying degree/severity of MGD. Severe Meibomian Gland Atrophy (Stage 4) will be excluded from the study. All patient data will be collected using the form shown in FIG. 1.

After the initial baseline evaluation, patients will receive daily doses of a dietary supplement containing 210 mg of C16:1n7-palmitoleate for 90 days. The clinical parameters of each patient will be reassessed at 3 months and 6 months following the baseline evaluation. Multivariate analysis will be performed by comparing meibomian gland atrophy parameters at baseline (Day 0), with those observed at 90 days and 180 days post treatment with C16:1n7-palmitoleate. Patient commentary regarding the subjective improvement of dry eye symptoms and objective indicia for meibomian gland atrophy will be analyzed.

It is predicted that at least some of the patients will show a reduction of meibomian gland atrophy after receiving the C16:1n7-palmitoleate dietary supplement These results will show that compositions comprising C16:1n7-palmitoleate, its derivatives, pharmaceutically acceptable salts thereof, or combinations thereof, are useful in treating meibomian gland atrophy in subjects with dry eye symptoms.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all FIGURES and tables, to the extent they are not inconsistent with the explicit teachings of this specification.

Other embodiments are set forth within the following claims.

What is claimed is:

1. A method for treating or reducing the risk of occurrence of dry eyes in a subject in need thereof comprising administering to the subject an effective amount of a composition comprising one or more of C16:1n7-palmitoleate, a C16:1n7-palmitoleate derivative, a pharmaceutically acceptable salt thereof, or a combination thereof; wherein the C16:1n7-palmitoleate derivative is a monoglyceride, diglyceride, triglyceride, free acid, a pharmaceutically acceptable salt, or ($C_1$-$C_8$) alkyl ester of C16:1n7-palmitoleate, and further wherein the composition is administered orally, topically, systemically, intravenously, subcutaneously, intraperitoneally, or intramuscularly.

2. The method of claim 1, wherein the composition further comprises a C16:0-palmitate, a C16:0-palmitate derivative, or a combination thereof; wherein the C16:0-palmitate derivative is a monoglyceride, diglyceride, triglyceride, free acid, a pharmaceutically acceptable salt, or ($C_1$-$C_8$) alkyl ester of C16:0-palmitate.

3. The method of claim 1, wherein the composition further comprises a C18:1n9-oleate, a C18:1n9-oleate derivative, or a combination thereof; wherein the C16:0-palmitate derivative is a monoglyceride, diglyceride, triglyceride, free acid, a pharmaceutically acceptable salt, or ($C_1$-$C_8$) alkyl ester of C16:0-palmitate.

4. The method of claim 1, wherein the subject has been diagnosed with dry eyes or dry eye syndrome.

5. The method of claim 1, wherein the subject is at risk for dry eyes or dry eye syndrome.

6. The method of claim 5, wherein the subject is human.

7. The method of claim 1, further comprising simultaneously, sequentially, or separately administrating at least one additional therapeutic agent, wherein the at least one additional therapeutic agent, is selected from the group consisting of cyclosporine ophthalmic emulsion, antibiotics, and hydroxypropyl cellulose insert.

8. The method of claim 1, wherein administration of the composition, treats, or ameliorates one or more signs and/or symptoms of dry eyes.

9. The method of claim 8, wherein the signs and/or symptoms are selected from the group consisting of stinging, burning, or scratchy sensation in the eyes, stringy mucus in or around the eyes, increased eye irritation from smoke or wind, eye fatigue, sensitivity to light, eye redness, sensation of foreign object in eyes, difficulty wearing contact lenses, periods of excessive tearing, swollen eyes, eye discomfort, eye pain, and blurred vision.

10. The method of claim 1, wherein the subject displays tear osmolarity less than 308 mOsms/L.

11. The method of claim 1, wherein the composition is administered daily for 4 weeks or more.

12. The method of claim 1, wherein the method comprises treating dry eyes in a subject.

13. The method of claim 1, wherein the method comprises reducing the risk of occurrence of dry eyes in a subject.

14. The method of claim 1, wherein the composition is administered orally.

15. The method of claim 14, wherein the composition comprises a dietary supplement.

* * * * *